(12) United States Patent
Gerson et al.

(10) Patent No.: US 9,993,668 B2
(45) Date of Patent: Jun. 12, 2018

(54) FACE MASK ASSEMBLY

(71) Applicant: Louis M. Gerson Co., Inc., Middleboro, MA (US)

(72) Inventors: Ronald L. Gerson, Middleboro, MA (US); Pierre LaPointe, Marlborough, MA (US)

(73) Assignee: Louis M. Gerson Co., Inc., Middleboro, MA (US)

( * ) Notice: Subject to any disclaimer, the term of this patent is extended or adjusted under 35 U.S.C. 154(b) by 452 days.

(21) Appl. No.: 14/735,631

(22) Filed: Jun. 10, 2015

(65) Prior Publication Data

US 2016/0361575 A1    Dec. 15, 2016

(51) Int. Cl.
| | |
|---|---|
| *A62B 18/02* | (2006.01) |
| *A62B 18/00* | (2006.01) |
| *A62B 18/08* | (2006.01) |
| *A62B 9/04* | (2006.01) |
| *A62B 7/00* | (2006.01) |
| *A62B 7/10* | (2006.01) |
| *A61M 16/06* | (2006.01) |
| *A62B 18/10* | (2006.01) |

(52) U.S. Cl.
CPC .......... *A62B 18/025* (2013.01); *A61M 16/06* (2013.01); *A62B 7/00* (2013.01); *A62B 7/10* (2013.01); *A62B 9/04* (2013.01); *A62B 18/00* (2013.01); *A62B 18/02* (2013.01); *A62B 18/08* (2013.01); *A62B 18/084* (2013.01); *A62B 18/10* (2013.01)

(58) Field of Classification Search
CPC .. A61M 16/00; A61M 16/06; A61M 16/0605; A61M 16/105; A62B 7/00; A62B 7/10; A62B 9/02; A62B 9/04; A62B 17/00; A62B 17/001; A62B 18/00; A62B 18/02; A62B 18/025; A62B 18/06; A62B 18/08; A62B 18/04; A62B 18/082; A62B 18/084; A62B 18/086; A62B 18/10
See application file for complete search history.

(56) References Cited

U.S. PATENT DOCUMENTS

| | | | |
|---|---|---|---|
| 5,794,617 A | 8/1998 | Brunell et al. | |
| 6,062,221 A | 5/2000 | Brostrom et al. | |
| 6,457,473 B1 | 10/2002 | Brostrom et al. | |
| 6,497,232 B2 * | 12/2002 | Fecteau ............... | A62B 18/084 128/201.24 |
| 6,715,490 B2 | 4/2004 | Byram | |
| 6,732,733 B1 | 5/2004 | Brostrom et al. | |
| 8,839,785 B2 | 9/2014 | Castiglione et al. | |

(Continued)

FOREIGN PATENT DOCUMENTS

WO    1995/007734    3/1995

*Primary Examiner* — Colin W Stuart
(74) *Attorney, Agent, or Firm* — Occhiuti & Rohlicek LLP

(57) ABSTRACT

A face mask is configured to be worn on a wearer's head and to cover the wearer's nose and mouth. The face mask includes a mask body having apertures, an inhalation port positioned within one of the apertures of the mask body, an exhalation valve positioned within a second one of the apertures of the mask body, a harness assembly configured to extend about a wearer's head wherein the harness assembly includes a first strap, a strap retainer positioned on the mask body and disposed over the exhalation valve, the strap retainer configured to receive the first strap; and a valve protector positioned between the first strap and the exhalation valve.

13 Claims, 3 Drawing Sheets

(56) References Cited

U.S. PATENT DOCUMENTS

| | | |
|---|---|---|
| 2002/0088466 A1 | 7/2002 | Brostrom et al. |
| 2005/0211251 A1 | 9/2005 | Henderson et al. |
| 2008/0156329 A1* | 7/2008 | Gerson ................ A62B 18/025 128/206.12 |
| 2010/0263673 A1 | 10/2010 | Kielow et al. |
| 2013/0319420 A1 | 12/2013 | Danford |

* cited by examiner

FACE MASK ASSEMBLY

This invention relates to respirators and face mask assemblies.

BACKGROUND

A respirator is a device designed to protect the wearer from inhaling harmful dusts, fumes, vapors, or gases. Respirators come in a wide range of types and sizes used by the military, private industry, and the public. All respirators have some type of facepiece or mask body held to the wearer's head with straps, a cloth harness, or some other method. The mask body of the respirator covers either the entire face ("Full Face Masks") or the bottom half of the face including the nose and mouth ("Half-Masks").

Half-face mask assemblies generally include an exhalation valve that opens in response to increased pressure when the wearer exhales to allow the exhaled air to be rapidly purged from the mask interior. The inhaled (contaminated) air flows through a filter element that is generally placed over inhalation ports to purify the air that is inhaled These inhalation ports also are generally fitted with a one-way valve that closes when the user exhales in order to preserve the filters from degradation by moisture exhaled in the wearer's breath and to direct all the exhalation air through the exhalation valve or diaphragm. It is desirable that the air path between the exhalation valve and the environment be free from blockage or impediments.

SUMMARY

The invention relates to a face mask configured to be worn on a wearer's head and to cover the wearer's nose and mouth. In a general aspect of the invention, the face mask comprises a mask body having a plurality of apertures, an inhalation port positioned within a first one of the plurality of apertures of the mask body, an exhalation valve positioned within a second one the plurality of apertures of the mask body, a harness assembly configured to extend about a wearer's head wherein the harness assembly includes a first strap, a strap retainer positioned on the mask body and disposed over the exhalation valve, the strap retainer configured to receive the first strap; and a valve protector positioned between the first strap and the exhalation valve.

Embodiments of this aspect of the invention may include one or more of the following features. The harness assembly is adapted for retaining the mask body at a first position covering a wearer's nose and mouth, and at a second position dropped down from a wearer's face without removing the harness assembly from a wearer's head. The face mask may further include a second strap and the strap retainer is configured to guide the first strap and a second strap in a crossed configuration, the first strap and second strap crossing at the valve protector. In some embodiments, the strap retainer includes a first engagement point and a second engagement point associated with the first strap as well as a third engagement point and fourth engagement point associated with the second strap. For example, the first engagement point is diagonally positioned from the third engagement point and the second engagement point is diagonally positioned from the fourth engagement point. In some examples, the first engagement point, second engagement point, third engagement point and fourth engagement point are each in the form of a slot. The strap retainer can include an opening such that when the strap retainer is positioned on the mask body and the face mask is positioned on the wearer's head, exhaust from the wearer is directed downward through the opening.

The mask body includes a deformable resilient face-shaped face piece having at least one outer wall carrying the exhalation valve and the inhalation valve and an encircling rim formed by the face piece shaped to contact and conform to the wearer's face to form a seal against the face when the face mask is positioned on the wearer. The encircling rim has an edge defined by outer face piece walls extending away from the rim, the face piece defining an interior portion of the face piece forming a breathing chamber, and an encircling bent back rim portion extending from the rim and toward the interior of the face piece.

The strap retainer can be configured to be detachably connected to the mask body. The strap retainer can include a first plurality of attachment elements and the exhalation valve housing includes a second plurality of attachment elements. With this arrangement, the valve protector includes a first plurality of slots configured to receive the first plurality of attachment elements in the strap retainer and a second plurality of slots configured to receive the second plurality of attachment elements in the valve housing.

The valve protector includes a first surface that is proximal to the strap retainer and a second surface proximal to the exhalation valve, the valve protector having an aperture positioned over the exhalation valve. In some embodiments, the valve protector can be configured to be detachably connected to the mask body and can be ring-shaped.

Other features and advantages of the invention are apparent from the following description, and from the claims.

DESCRIPTION

Figure 1:
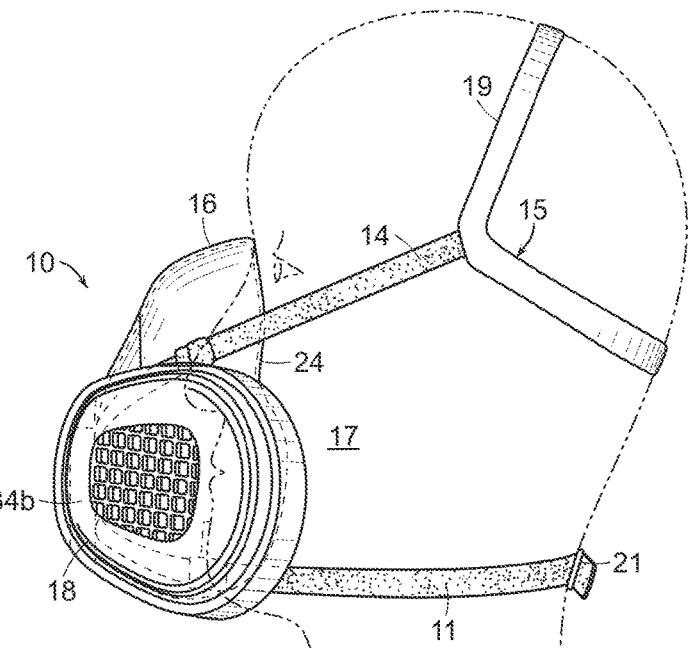
FIG. 1 is a side view of a face mask assembly worn on a wearer's head.

Referring to FIG. 1, a representative face mask 10 is shown held against a wearer's face 17 with a harness assembly 15 having a right adjustable strap 12, a left adjustable strap 14 and a lower adjustable strap 11 so that a face piece 16 having a face shaped flange rim 24 covers and seals the user's nose and mouth. Right strap 12 and left strap 14 are attached to a head cradle 19 while lower strap 11 is attached to a release buckle 21. When the mask is worn, the user inhales filtered ambient air through preferably removably mounted conventional filters 18, which are positioned on the sides of the face mask, and exhales air through a conventional flapper and exhalation valve 34 (FIG. 2) at the front of the mask. To comfortably conform to the user's face, face piece 16 is preferably made at least in part from a soft, deformable, preferably resilient or elastomeric material, and can be made in various sizes to accommodate different users.

As will be discussed in greater detail below, harness assembly 15 with its right and left adjustable straps 12, 14, is configured to attach to face mask 10, through a strap retainer 40 (discussed in greater detail below), such that the face mask can be easily adjusted and to conform to different wearer's faces. The configuration also allows the face mask 10 to be moved between multiple positions without removing the harness assembly. For example, face mask 10 can be worn at a first position with the face piece 16 and face shaped rim 24 covering and sealing the user's nose and mouth. In a second position, face mask 10 can be dropped from the wearer's face to a second position without moving the harness assembly from the head of the wearer. If the wearer is using, for example, a protective hard-hat, this is a particularly desirable feature. In this second position, face mask 10 hangs near the wearer's body in a dropped down position. This is advantageous in situations where the wearer needs to access his or her mouth (e.g., to speak) or otherwise needs to remove the face mask without having to remove the face mask altogether and then reposition the face mask over the wearer's mouth and nose when work recommences. Also, in the second position, face mask 10 hangs off of the wearer's body so that does not have to be placed on the ground or stored elsewhere.

Face piece 16 is in the form of a deformable resilient face-shaped member having an outer wall that supports the exhalation valve housing and inhalation valves as well as an encircling rim formed by the face piece that is shaped to contact and conform to the wearer's face thereby forming a seal against the face when the face mask is positioned on the wearer. The encircling rim has an edge defined by outer face piece walls extending away from the rim. The face piece 16 defines an interior portion of the face piece that forms a breathing chamber, and an encircling bent back rim portion 23 extending from the encircling rim and toward the interior of the face piece.

Face piece 16 is made from a molded polymeric elastomeric material as by compression, injection or vacuum molding of materials, such as polyvinylidene chloride, natural rubber, synthetic rubbers such as silicone, neoprene, PVC, or urethane.

Figure 2:
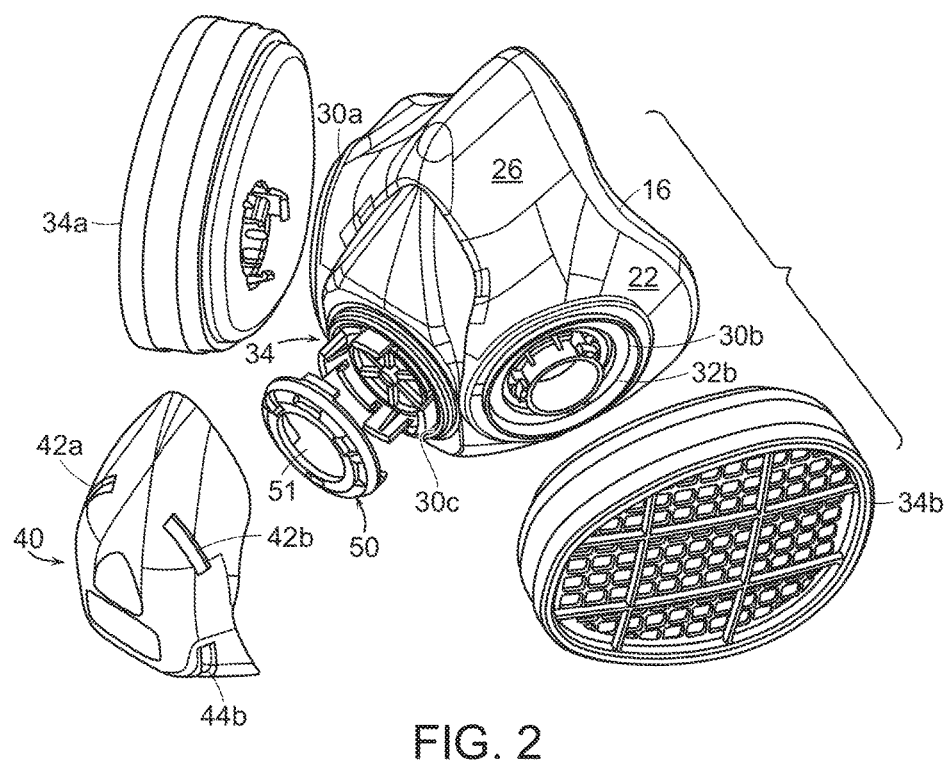
FIG. 2 is a front, exploded perspective view of the face mask assembly of FIG. 1 (without harness assembly).
Figure 3:
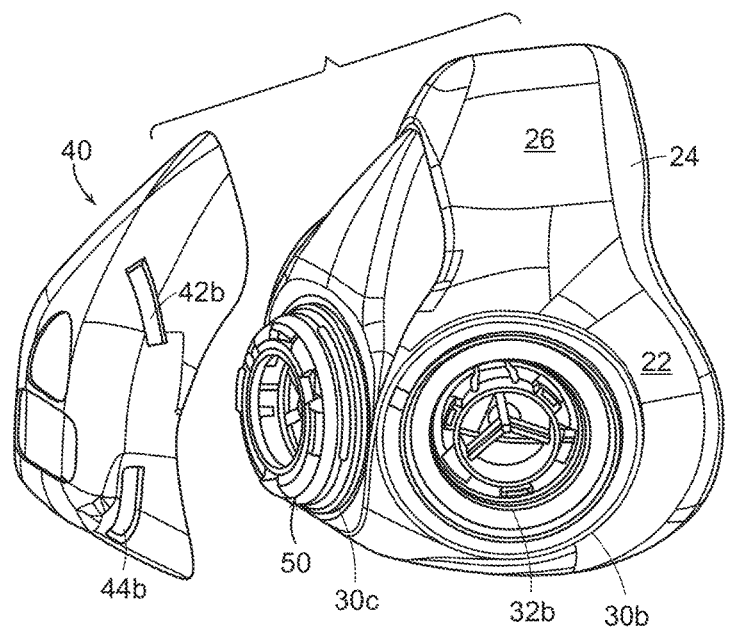
FIG. 3 is a partially exploded perspective view of the face mask assembly of FIG. 1.

Referring to FIGS. 2 and 3, face piece 16 has a preferred thickness between about 0.015 to 0.125 inches, and is preferably at least about 0.032 inches. The thickness can vary within a single face piece from about 0.032 at the inner edges of the bent back portion 26 to provide greater flexibility, to about 0.125 at the outer sides 22 where greater support is needed. At such thickness and selected durometer, the material of the bent back portion 26 has sufficient durability, softness, and deformability to comfortably form a good seal with the face of a user, while not being too flimsy.

Face piece 16 has a pair of side apertures 30a, 30b, one on each side of face piece 16 with a third aperture 30c positioned between the side apertures. Apertures 30a, 30b are sized and shaped to receive corresponding inhalation valves 32a, 32b which are configured to receive removable filter cartridges 34a, 34b for filtering particulates and/or gases. As can be seen in FIG. 2, filter cartridges 34a, 34b are of the type that uses a bayonet mount arrangement for attaching to face piece 16. Third aperture 30c is sized and shaped to receive an exhalation valve 34 such that when face mask 10 is placed on the wearer's face, exhalation valve is positioned over the wearer's mouth. Exhalation valve 34 is of the type having a flexible diaphragm.

Face mask 10 includes a strap retainer 40 that is adapted to attach to face piece 16 and over exhalation valve 34. Strap retainer 40 is in the form of a concave shell for accommodating exhalation valve, as well as straps 12, 14 and attachment elements 48, configured to be received by corresponding slots 56 in the valve protector 50. When strap retainer 40 is positioned on face piece 16 the two components conform to provide a unitary, smooth and contoured face mask 10. Strap retainer 40 is configured to receive and support straps 12, 14 at four points of engagement. The four engagement points are in the form of a pair of upper slots 42a, 42b and a pair of lower slots 44a, 44b. Each of the upper slots 42a, 42b and lower slots 44a, 44b are rectangular in shape and suitably sized to allow right strap 12 and left strap 14 to pass through without resistance. Strap retainer 40 includes at its lower end an opening 46 through which air from exhalation valve 34 is expelled. Opening 46 is positioned on strap retainer 40 such that when face mask 10 is in use, the opening is directed in a downward direction. Positioned in this way, the diaphragm in the exhalation valve is covered and the chance for debris, fragments, paint overspray or other particulates (entering the mask and contaminating the exhalation diaphragm is minimized.

Figure 4:
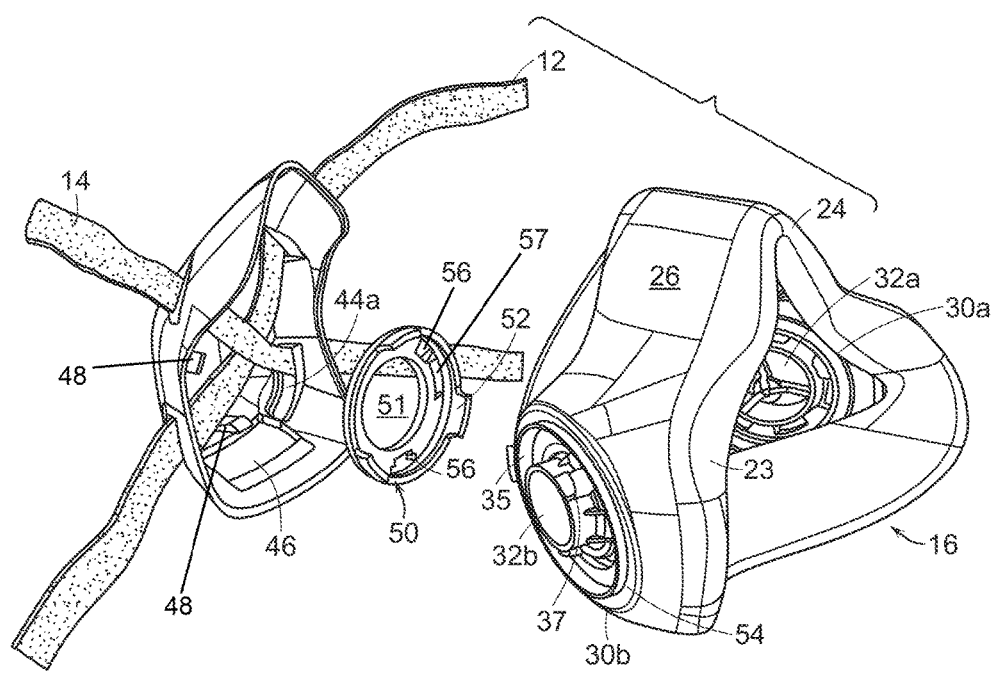
FIG. 4 is a rear, exploded perspective view of the face mask assembly of FIG. 1 showing the configuration of straps and strap retainer.

Referring to FIG. 4, right strap 12 and left strap 14 extend through upper slots 42a, 42b and lower slots 44a, 44b in crosswise fashion. Right strap 12 and left strap 14 extend in crosswise fashion because generally there is not sufficient space between opening 30c for supporting the exhalation valve 34 and cartridges 34a and 34b when they are positioned on inhalation valve apertures 30a, 30b for them to run vertically, rather than crosswise, through the slots. In particular, right strap 12 extends through upper slot 42a and lower slot 44b while left strap 14 extends through upper slot 42b and lower slot 44a. With this arrangement, there is a risk that right strap 12 and left strap 14 can contact and impede airflow through a diaphragm flapper of exhalation valve 34, particularly at the intersection of the straps between the exhalation valve and the inner surface of strap retainer 40.

Figure 5:
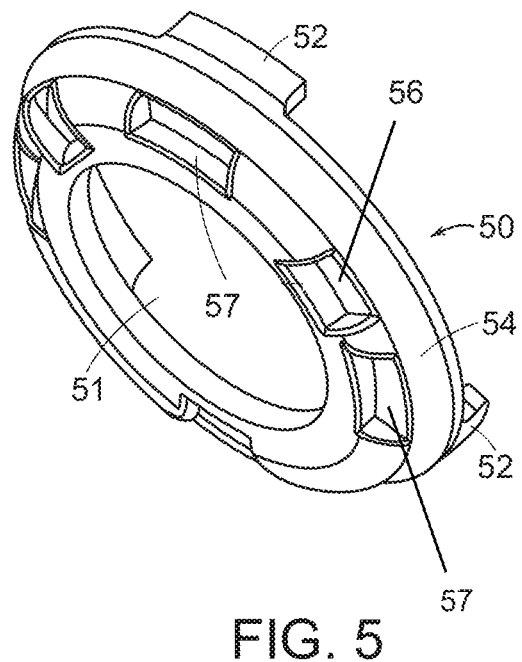
FIG. 5 is a front perspective view of the valve protector of FIG. 1.

Referring to FIGS. 2, 4 and 5, to ensure adequate airflow and to minimize the possibility that right strap 12 and left strap 14 block the air path to exhalation valve 34, face mask 10 includes a valve protector 50. Valve protector 50 is dome-shaped such that the straps will be prevented from contacting and paced from the front surface of exhalation valve 34, and is in the form of a ring (ring-shaped) that defines an aperture 51 over the exhalation valve. Valve protector 50 includes a set of radially-spaced tabs 52 positioned on a peripheral wall 54, each tab 52 being sized and configured to engage an outer lip of exhalation valve 34. Exhalation valve housing 35, in turn, includes a set of radially-spaced tabs 37 that are sized and configured to be received within appropriately sized and shaped radial slots 57 of valve protector 50.

It is to be understood that the foregoing description is intended to illustrate and not to limit the scope of the invention, which is defined by the scope of the appended claims. For example, although the harness assembly is described as having a pair of separate straps, in certain embodiments, a single strap can be used with the strap retainer. Other embodiments are within the scope of the following claims.

What is claimed is:

1. A face mask configured to be worn on a wearer's head and to cover the wearer's nose and mouth, the face mask comprising:
   a mask body having a plurality of apertures;
   an inhalation port positioned within a first one of the plurality of apertures of the mask body;
   an exhalation valve positioned within a second one of the plurality of apertures of the mask body;
   a harness assembly configured to extend about the wearer's head wherein the harness assembly includes a first strap;

a strap retainer positioned on the mask body and disposed over the exhalation valve, the strap retainer configured to receive the first strap; and a valve protector positioned between the first strap and the exhalation valve wherein the strap retainer includes a first plurality of attachment elements, the exhalation valve includes a second plurality of attachment elements, and the valve protector includes a first plurality of slots configured to receive the first plurality of attachment elements and a second plurality of slots configured to receive the second plurality of attachment elements.

2. The face mask of claim 1 wherein the harness assembly is adapted for retaining the mask body at a first position covering the wearer's nose and mouth, and at a second position dropped down from the wearer's face without removing the harness assembly from the wearer's head.

3. The face mask of claim 1 further comprising a second strap and the strap retainer is configured to guide the first strap and the second strap in a crossed configuration, the first strap and the second strap crossing at the valve protector.

4. The face mask of claim 1 wherein the strap retainer includes:
   a first engagement point and a third engagement point associated with the first strap and;
   a second engagement point and fourth engagement point associated with a second strap.

5. The face mask of claim 4 wherein the first engagement point is diagonally positioned from the third engagement point and the second engagement point is diagonally positioned from the fourth engagement point.

6. The face mask of claim 4 wherein the first engagement point, second engagement point, third engagement point and fourth engagement point are each in the form of a slot.

7. The face mask of claim 4 wherein the mask body includes:
   a deformable resilient face shaped face piece having at least one outer wall carrying the exhalation valve and the inhalation port; and
   an encircling flange formed by the face piece shaped to contact and conform to the wearer's face to form a seal against the face when the face mask is positioned on the wearer.

8. The face mask of claim 1 wherein the strap retainer includes an opening such that when the strap retainer is positioned on the mask body and the face mask is positioned on the wearer's head, exhaust from the wearer is directed downward through the opening.

9. The face mask of claim 1 wherein the mask body includes a face shaped face piece, wherein an encircling flange has an edge defined by outer face piece walls extending away from the encircling flange, the face piece defining an interior portion of the face piece forming a breathing chamber, and an encircling bent back rim portion extending from the encircling flange and toward the interior portion of the face piece.

10. The face mask of claim 1 wherein the strap retainer is configured to be detachably connected to the mask body.

11. The face mask of claim 1 wherein the valve protector includes a first surface that is proximal to the strap retainer and a second surface proximal to the exhalation valve, the valve protector having an aperture positioned over the exhalation valve.

12. The face mask of claim 1 wherein the valve protector is configured to be detachably connected to the mask body.

13. The face mask of claim 1 wherein the valve protector is ring-shaped.

* * * * *